(12) United States Patent
Pearl et al.

(10) Patent No.: US 6,497,719 B2
(45) Date of Patent: Dec. 24, 2002

(54) APPARATUS AND METHOD FOR STIMULATING HAIR GROWTH

(76) Inventors: Henry Pearl, 17244 Hampton Blvd., Boca Raton, FL (US) 33496; David Sinofsky, 17244 Hampton Blvd., Boca Raton, FL (US) 33496

(*) Notice: Subject to any disclaimer, the term of this patent is extended or adjusted under 35 U.S.C. 154(b) by 0 days.

(21) Appl. No.: 09/882,724

(22) Filed: Jun. 15, 2001

(65) Prior Publication Data

US 2002/0128696 A1 Sep. 12, 2002

Related U.S. Application Data

(60) Provisional application No. 60/273,701, filed on Mar. 6, 2001.

(51) Int. Cl.[7] ............................................... A61N 5/067
(52) U.S. Cl. ............................................ 607/89; 607/88
(58) Field of Search ................................... 607/88–89

(56) References Cited

U.S. PATENT DOCUMENTS

| | | | |
|---|---|---|---|
| 2,397,757 A | | 4/1946 | Schwedersky |
| 4,653,495 A | | 3/1987 | Nanaumi |
| 5,103,073 A | | 4/1992 | Danilov et al. |
| 5,303,722 A | * | 4/1994 | Godfrey et al. ............. 132/212 |
| 5,306,143 A | | 4/1994 | Levy |
| 5,569,368 A | * | 10/1996 | Larsky et al. ............... 132/148 |
| 5,569,929 A | | 10/1996 | Mizutani et al. |
| 5,616,140 A | | 4/1997 | Prescott |
| 5,803,093 A | * | 9/1998 | Romano ..................... 132/114 |
| 5,814,078 A | | 9/1998 | Zhou et al. |
| 6,022,345 A | | 2/2000 | Miller et al. |
| 6,129,748 A | | 10/2000 | Kamei |
| 6,187,029 B1 | | 2/2001 | Shapiro et al. |

FOREIGN PATENT DOCUMENTS

| | | |
|---|---|---|
| DE | 3336939 A1 | 4/1985 |
| DE | 3511281 A1 | 4/1986 |
| EP | 0139278 A1 | 5/1985 |
| FR | 2518412 | 6/1983 |
| WO | WO 01/60457 | 8/2001 |

OTHER PUBLICATIONS

Website www.lasercomb.net for Hairmax LaserComb by Lexington International.*

* cited by examiner

Primary Examiner—Roy D. Gibson
Assistant Examiner—Henry M. Johnson
(74) Attorney, Agent, or Firm—John C. Smith

(57) ABSTRACT

A hand-held laser device that stimulates hair growth. The device provides distributed laser light to the scalp while simultaneously parting the user's hair to ensure that the laser light contacts the user's scalp. A unique beam splitting reflector splits a single laser beam to ensure that energy from the laser beam is evenly distributed. The reflector is mechanically aligned with the laser source and has a zigzag structure which mechanically deflects portions of the beam as it passes over the peaks of the reflector. The portions of the laser beam form a line of laser beams that project toward the user's scalp. Parallel rows of teeth are aligned with a central row of individual laser beams and part the user's hair to form furrows in the user's hair as the device is combed through the user's hair. The furrows create an unobstructed path for the laser beam to reach the scalp of the user.

20 Claims, 12 Drawing Sheets

APPARATUS AND METHOD FOR STIMULATING HAIR GROWTH

CROSS-REFERENCE TO RELATED APPLICATIONS

This application is related to the commonly owned copending application entitled "Apparatus and Method for Stimulating Hair Growth," filed Mar. 6, 2001, bearing U.S. Ser. No. 60/273,701 and naming Henry Pearl and David Michael Sinofsky, the named inventors herein, as sole inventors, the contents of which is specifically incorporated by reference herein in its entirety. This application is further related to the commonly owned co-pending PCT application entitled "Improved Laser Comb Design/Function," filed Apr. 11, 2000, bearing PCT Application Ser. No. PCT/AU00/00302 and naming Henry Pearl, one of unnamed inventor's herein as sole inventor, the contents of which is specifically incorporated by reference herein in its entirety.

BACKGROUND OF THE INVENTION

1. Technical Field

The present invention relates to a method and apparatus for treating alopecia, hair loss, and loss of hair color (greying). In particular, it relates to a method of treating the scalp or skin of an individual to increase blood flow and general health of the skin to promote the healthier growth of hair and restoration of hair color.

2. Background Art

The loss of hair has traditionally been a problem for a substantial percentage of the population. Whether the problem is alopecia (male pattern baldness) or thinning hair, the individuals affected will generally find this to be distressing and detrimental to their appearance. In addition, the loss of hair will often make individuals appear to be older than they are. For this reason, a variety of attempts have been made to improve an individual's appearance by restoring the appearance of a full head hair.

Early attempts to address this problem focused on the use of hair pieces (i.e. toupees or wigs). While these devices provided some degree of success, they have several drawbacks. In particular, they often have an unnatural appearance which allows them to be easily detected, even from a distance, by other individuals. In order to make one of these devices appear to be the natural hair of the wearer, they must be constructed in a fairly expensive manner using real human hair which is matched in color to the individual's remaining hair. Unfortunately, many individuals cannot afford a high quality hair piece such as this, and settle for a lower quality hair piece fabricated from synthetic fibers.

In addition, hair pieces have the additional drawback that they may be inconvenient to use in situations, such as swimming, where they may become damaged or loosened. In this situation, the individual may be embarrassed due to the failure of the device. It would be desirable to improve the appearance of an individual's hair without having to resort to hair pieces fastened to an individual's head which are expensive and occasionally prone to failure due to environmental circumstances.

Those skilled in the art will recognize that more complicated mechanical solutions such as "hair weaving" exist. These more complicated solutions typically have the same drawbacks and problems as those associated with hair pieces. In addition, they are often more expensive than conventional hair pieces.

Another attempt to address this problem has been to surgically replace missing hair with "hair plugs." This surgical solution overcomes the problems created by the use of hair pieces in that the replacement hair plugs use the real hair of the individual, which results in a perfect color match and a natural appearance. In addition, the individual has no restrictions, such as those discussed above in regard to swimming and other activities, which were discussed in regard to hair pieces. Unfortunately, this method of treating hair loss is expensive, and requires the use of medical professionals for the surgical hair transplant procedure. As a result, this procedure may not be available to a substantial portion of the public due to its high cost. It would be desirable to have a method of facilitating the growth of hair which was economically available to a substantial part of the entire public.

In addition to hair pieces and surgical transplants, pharmaceutical products have also been developed to encourage hair growth. These products can take the form of ingestible medications or topical skin treatments. The ingestible medications have been proven to encourage hair growth, but they have several significant drawbacks. In particular, they are typically prescription medications which require the cost and inconvenience of visiting a physician. In addition, the fact that they are prescription medications typically means that they will have a higher cost than non-prescription drugs. Perhaps more important than the issue of cost is the potential side effects of ingestible drugs. Quite often, the use of this type of ingestible medications may result in serious health side effects, such as damage to the individual's liver, or other internal organs, or present other serious side effects. It would be desirable to have a method of stimulating hair growth which did not carry the risks of side effects inherent in ingestible pharmaceutical medications.

Another type of pharmaceutical medication has been the use of topical skin treatments. This type of medication is often similar to prescription medications with the same cost disadvantage of ingestible medications. While some are now available as over the-counter preparations, they typically have a reduced strength and are less effective than are their prescription counterparts. In addition, they typically have to be applied every day to achieve and maintain their desired results. It would be desirable to have an effective low-cost method of stimulating hair growth which did not require potential visits to a physician, a continuous use of expensive medications, and daily treatments to ensure results.

Progressively, over the last 25 years, mainly in Europe and Asia, scientists have found that lasers can be used to stimulate hair growth. Devices have been developed having structures similar to a large floor mounted, or chair mounted, helmet. These devices contain multiple laser assemblies, and are designed to irradiate the individual's entire scalp and hair with laser energy. It is been found that there are several disadvantages associated with this approach. In particular, these are typically very large and expensive commercial devices which are found in beauty salons and spas. In order to take advantage of them, an individual will go to the establishment for the devices located and pay for treatments on a per treatment basis. Over time, this represents a fairly expensive proposition for the individual, and typically requires a trained operator to be present and to conduct the treatment.

In addition, the helmet-like structure of this device creates an additional disadvantage. Since the device covers the head of the individual, a substantial portion of the laser energy which is intended for application to the individual's scalp is blocked by the hair of the individual, thinning though it may be, which effectively forms a canopy over the individual's scalp. It would be desirable to have an inexpensive method of applying laser treatments which does not require an individual to go to a specific location where large laser devices are used, which does not require the individual to pay every time a laser treatment is taken, and which maximizes the amount of laser energy applied to the scalp while minimizing the amount of laser energy which is blocked by the individual's hair. Likewise, it would be desirable to have a laser treatment device which has a relatively small number of lasers, and which could apply laser energy to the individual's scalp without interference by the individual's hair.

Another problem associated with hair is the loss of hair color (i.e. greying) which has the effect of making an individual appear to be older. Individuals often attempt to treat this problem by dying their hair. Unfortunately, this method of treatment has several disadvantages. For example, as was the case with hair pieces, discussed above, it can be difficult to produce the proper hair color which may make it obvious that the hair was dyed. In addition, the dyed hair tends to fade over time which results in re-appearance of the grey hair and a persistent change in color. Individuals who dye their hair typically have to re-dye their hair periodically. Of course, this represents an ongoing expense and inconvenience to the individual. Further, unless the dying process is performed by a trained individual, the results may be undesirable and unattractive. This further increases the cost of hair dying due to the need to hire a trained professional to perform the process. It would be desirable to have a method of treating loss of hair color without having to have an ongoing expense for dyes, or an ongoing expense for trained professionals to apply the dyes, and an ongoing inconvenience.

While providing several methods of treating alopecia, hair loss, and greying, the prior art has failed to provide an apparatus which is inexpensive to manufacture, has a minimum number of components, minimizes the amount of laser energy blocked by an individual's hair, and can be used without leaving the individual's home or using costly commercial equipment and trained personnel.

SUMMARY OF THE INVENTION

The present invention is a hand-held laser device for stimulating human hair growth. The device is used by the individual and does not require trained personnel to provide a treatment. The device provides laser light to the scalp while simultaneously parting the user's hair to ensure that the laser light contacts the user's scalp. A unique, stepped, beam splitting reflector splits a single laser beam to allow an individual laser to simultaneously provide multiple laser beams which are distributed across a segment of an individual's scalp. The reflector is mechanically aligned with the laser source and has a zigzag structure which mechanically deflects portions of the beam as it passes over the peaks of the reflector. The portions of the laser beam form a line of laser beams that project toward the user's scalp. Parallel rows of teeth are aligned with a central row of individual laser beams and part the user's hair to form furrows in the user's hair as the device is combed through the user's hair. The furrows create an unobstructed path for the laser beam to reach the scalp of the user. Identical rows of teeth are placed on either side of the line of laser beams to allow the device to be combed through the user's hair in either direction.

DESCRIPTION OF THE PREFERRED EMBODIMENT

Figure 1A:
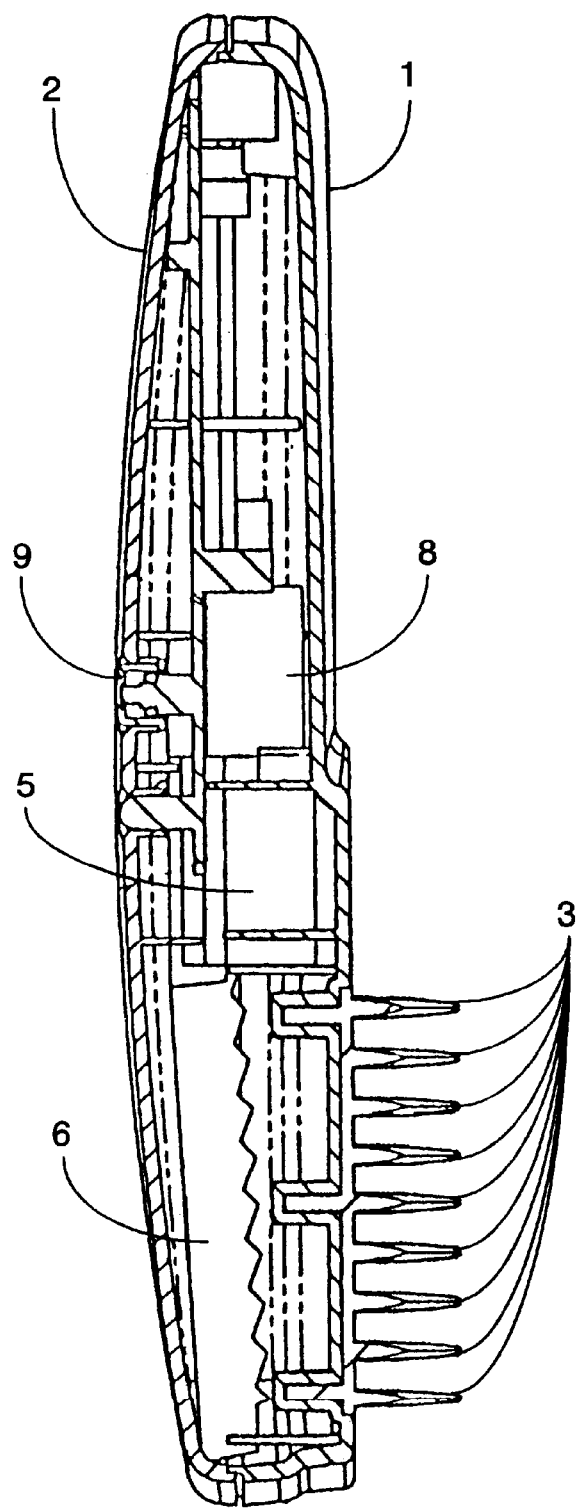
FIG. 1A is a side cutaway view of a preferred embodiment of the invention which illustrate a row of furrow forming teeth extending outward from the device, the laser beam generator, and a zigzag beam splitting reflector.

Prior to a detailed discussion of the figures, a general overview of the system will be presented. For ease of discussion, the term "scalp" will be used to describe the conventional definition which describes the hair covered portion of skin on the user's head, and in addition, any skin surface where hair is desired to be grown (e.g. the beard, etc).

It has been found that low-power lasers may be used in a variety of therapeutic applications. For example, low-power lasers are used widely for a variety of cosmetic applications such as skin care, scar reduction, wound healing and the like. In addition, it has also been found that the application of low-power laser light to an individual's scalp will assist the hair's natural ongoing replacement process and improve the scalp's condition.

One of several factors associated with the use of lasers to stimulate hair growth is that laser treatments tend to increase scalp blood circulation. In fact, studies have shown that the application of laser energy to the scalp of a user can increase scalp blood circulation by more than fifty percent without significant changes in scalp temperature. This results in the skin receiving a more abundant supply of nutrients, and in turn, the structures in the skin, such as hair follicles, also receive a more abundant supply of nutrients and necessary materials from the body.

Microscopic studies have shown laser energy increases circulation and oxygenation of the blood to the scalp and hair bulb; removes calcification and blockages around the hair bulb; as well as increases cell replacement or regenerative activity. These factors help hair to improve in fullness, shine, body and elasticity. Problems such as over-oily or dry scalp, dandruff and itchiness can also be reduced. Research on the use of cold beam lasers indicates that application of a cold beam laser to an individual's scalp will normalize metabolism of tissues, improve trophism (blood cell nutrition), and assure a regular sebaceous secretion. Measurements taken from scalps treated by cold laser indicate that hair bulbs are strengthened, hair growth can be measurably ascertained, and hair color will darken.

The increase in blood flow helps as follows: in the human scalp, the follicles in which the hair grows is attached to the scalp by a structure known as the Papilla. The Papilla provides a path for nutrients in the blood to reach the cells in the hair. The laser treatment described herein improves both the condition of the Papilla itself, as well as the blood flow reaching the Papilla. The unique structure of the handheld device presented herein provides an unobstructed laser path to the Papilla which results in the scalp being bathed in laser light.

Another factor associated with the use of lasers is "energization." Energization can be explained as follows: Light is energy. The use of a laser light on scalp and hair follicles provides high levels of light which are used by a the cells in the scalp and hair to assist in the normal chemical processes performed by those cells. The scientifically agreed-upon term for this is photobiostimulation. The most common example of light converting into chemical energy is photosynthesis, where plants are fed via light converted into chemical energy. In a similar way, laser penetrates into soft tissue and increases the action of adenosine triphosphate (ATP), a molecule that is a major carrier of energy from one reaction site to another in all living cells. By doing so, laser light increases the energy available to cells so they take in nutrients faster and get rid of waste products. Because of this benefit, scientists and physicians have been using low level laser over the past 30 years to accelerate wound healing and regenerate tissue.

Yet another factor associated with the use of laser light is known as "vibration." Soft tissue and fluids in our bodies actually vibrate. The vibration occurs within a frequency range similar to that of cold-beam, red-light laser. In fact, one scientific theory holds that cells are largely dependant for healthy function on an exchange of energy and information with surrounding cells. This is achieved via individual wave systems by which cells communicate through inter-connective plasma by vibration. A cell is in an unhealthy state when its vibrations become irregular or out-of-step with this common communications system. However, it can be brought back into vibratory "harmony" by being irradiated with low level laser working at quantum level.

While the benefits of low-power laser treatments are known, attempts to take advantage of laser technology for the purpose of stimulating hair growth has produced limited results. In particular, when there is existing hair growth on the scalp being treated, as would be the case for individuals with thinning hair who are balding or experiencing alopecia, conventional laser beam devices do not satisfactorily penetrate the hair. As a result of the pre-existing hair blocking the path of the laser beam when it is aimed at the scalp, the effectiveness of the laser treatment is substantially reduced.

Another problem related to prior art laser treatment devices is that they tend to be large devices which are heavy and immobile. As a result, they would usually be found in a salon or clinic where the user would be charged each time the user obtained a treatment. Further, since these devices typically have fixed locations, they would not be available to the user when traveling, and they would be inconvenient to access even when the user was not traveling.

Prior art attempts to provide handheld devices have resulted in many undesirable drawbacks. For example, these devices tend to be large, bulky and complex due to the use of multiple laser modules and/or fiber optics which each produce a laser beam directed at a user's scalp. These devices also are difficult to manufacture due to the need to align the multiple lasers, or, in the case where fiber optics are used, to convey the laser energy into each fiber-optic by way of a complex lens system.

The invention provided herein solves all of the foregoing problems. The invention is a handheld, comb-like device which emits a row of laser beams which are produced by a single laser beam generator and then split into multiple laser beams by a zig-zag shaped reflector. Each laser beam in the row of laser beams has a pair of teeth which are positioned in regard to the laser beam such that as the handheld device is pulled through the individual's hair, one tooth parts the hair in front of the laser beam and the second tooth follows the laser beam holding the hair apart. By moving the hair in this manner, the two rows of teeth function to form furrows in the hair, thereby exposing the scalp of the user to the laser beam. This eliminates interference with the laser beam by the individual's hair and provides more laser energy directly to the scalp of the individual.

First, it overcomes the problem caused by pre-existing hair interfering with the laser beams by placing the laser beam generator between two rows of teeth which create "parts" in the user's hair which are aligned with individual laser beams generated by the device. As a result of this aligned parting of the user's hair, the pre-existing hair is moved out of the way of the laser beam and the user's scalp receives the full benefit of the laser treatment.

The ability to provide multiple beams from a single laser source is provided by a unique "zig-zag" lens which splits a single laser beam generated from a single laser device into multiple parallel beams. Each beam having a power level substantially similar to adjacent beams due to their generation by a single laser source. Likewise, the use of the zigzag lens has a beam reflector eliminating alignment problems which would be inherent in systems using multiple lasers.

In this invention, the preferred means by which the laser energy reaches the scalp is by way of a row of laser beams being preceded by a row of teeth that part the hair to expose the skin in advance of the row of laser beams. The row of teeth are aligned with the laser beams such that each tooth proceeds in advance of its respective beam to part the hair in front of the beam (i.e. forming a furrow) thereby ensuring that the beam is directed to the scalp and not blocked by the user's hair. In addition, the laser beams are followed by a second row of teeth which are also aligned with the row of laser beams. This second row of teeth allows the comb to be used in either direction for the convenience of the user. The second row of teeth also provides the benefit of keeping the hair parted for a slightly longer period of time to ensure that the hair does not fall back in place too quickly after the first row of teeth passes through the hair.

A more detailed discussion of the figures now follows.

FIG. 1A is a side cutaway view of a preferred embodiment of the invention that illustrates the arrangement of components in the device. The components of the device are held together and supported by a lower housing 1 and an upper housing 2. Two rows of teeth 3 (only one is shown in this figure) extends down from a lower housing 1. During use, the teeth 3 are combed through the user's hair in the same manner as an ordinary comb would be used. Also shown in this figure are a laser module 8, a switch 9, a coupling assembly 5, and a laser beam splitter/reflector 6.

This unit is designed to be a self-contained, handheld, device which applies a low-level laser beam directly to the scalp of a user without having the hair of the user interfere with the laser beam. In use, the user brushes the teeth 3 through the user's hair in the same manner as the user would use a hair brush. A laser beam is aligned with each of the teeth 3 in the device such that the laser beam follows the "furrow" created by the teeth 3 as they move through the user's hair. By parting the hair in front of the laser beam in this manner, the laser beam is able to reach the bottom of the furrow (i.e. the scalp) without interference from the hair. This is a substantial improvement over prior art techniques which used helmet-like structures to direct laser energy directly to the user's head without taking into consideration the fact that most of the laser beam energy would be prevented from reaching the user's scalp by the user's hair.

Figure 1B:
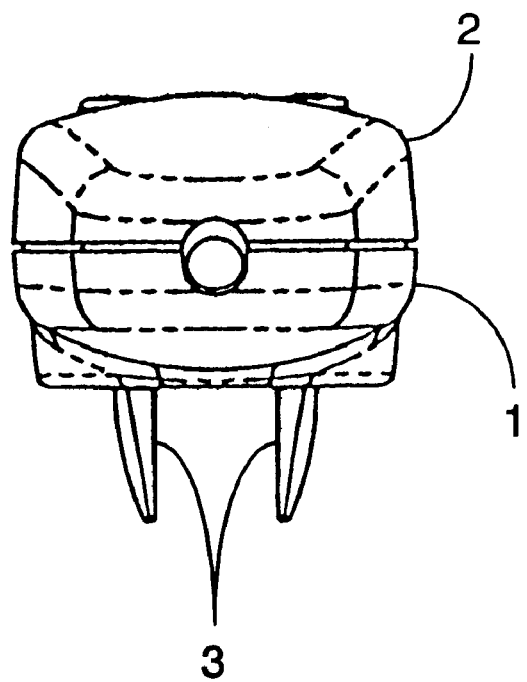
FIG. 1B is an end view of a preferred embodiment of the device which shows opposing furrow forming teeth extending outward from either side of the device.

FIG. 1B shows an end view of the device of FIG. 1A which illustrates that there are two parallel rows of teeth 3 projecting downward from the bottom housing 1. The laser beams project outward from the device between the two rows of teeth 3. Further, they are aligned with the teeth 3 such that the laser beam is projected into the furrow when the handheld device is moved in either direction across the user's scalp.

Figure 1C:
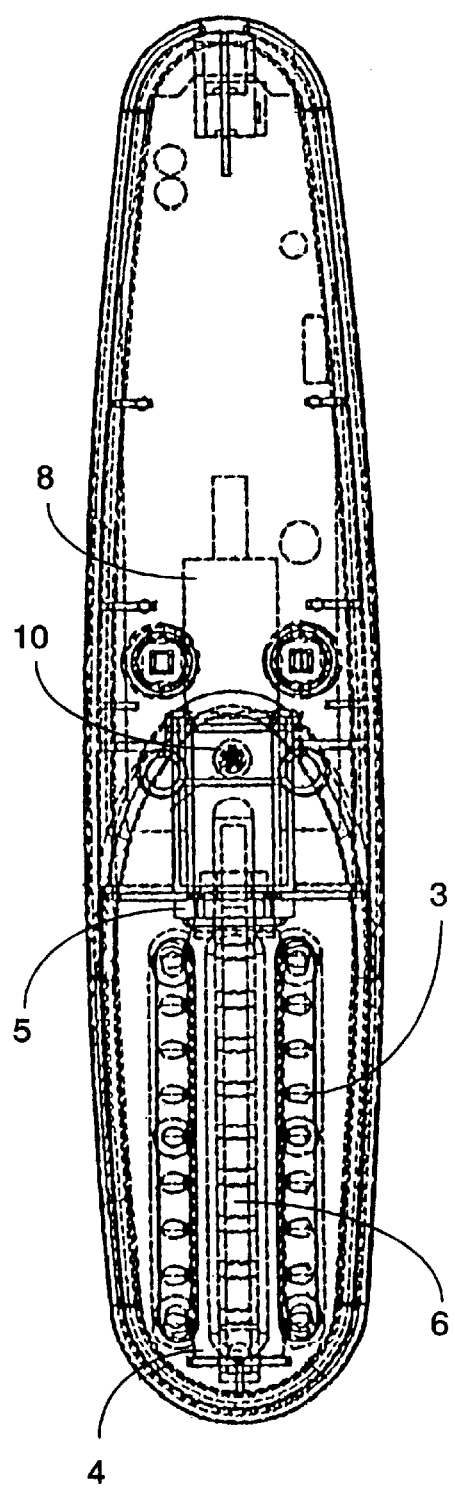
FIG. 1C is a bottom view of a preferred embodiment of the device which illustrates the two opposing rows of furrow forming teeth and the zigzag beam splitting reflector aligned with the opposing rows of furrow forming teeth.

FIG. 1C illustrates a bottom transparent view of the preferred embodiment of FIGS. 1A–B. In this view, the position and alignment of the laser reflector 6 is shown. The laser reflector 6 is placed between the two rows of teeth 3 such that, whether the it handheld device is moved forward or backward across the scalp, there is always a tooth 3 available in front of each laser beam to ensure that a furrow is created for each laser beam to reach the scalp. This results in a more effective application of laser energy to the scalp than was heretofore possible in prior art devices.

In addition to being more effective than prior art devices in terms of the actual application of laser energy to the scalp, the embodiment disclosed herein is also superior to prior art devices in that it is extremely lightweight and portable. It can be manufactured such that it is plugged into a wall socket for electrical energy, or alternatively, it can be battery operated to further add to the user's convenience. In addition, the reflector 6 allows a single laser to be used rather than the multiple lasers used by prior art devices.

Figure 2A:
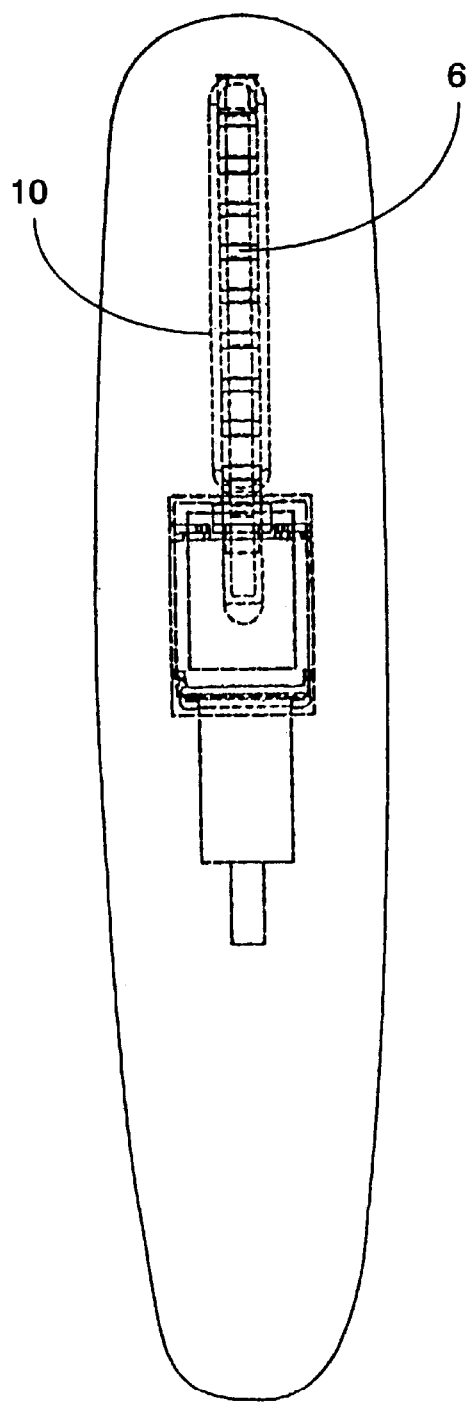
FIG. 2A is a bottom view of a preferred embodiment of the device which illustrates the zigzag beam splitting reflector attached to the laser beam generator.

In FIG. 2A, a bottom transparent view of a preferred embodiment of the handheld device is illustrated. For ease of discussion, several items have been eliminated from this figure which is intended to show the relative position of the reflector 6 in relation to a window 10. The window 10 provides a transparent cover for the reflector 6. This allows the reflector 6 to be sealed within the handheld device to protect it from contamination such as dust, water vapor, water, etc.

Figure 2B:
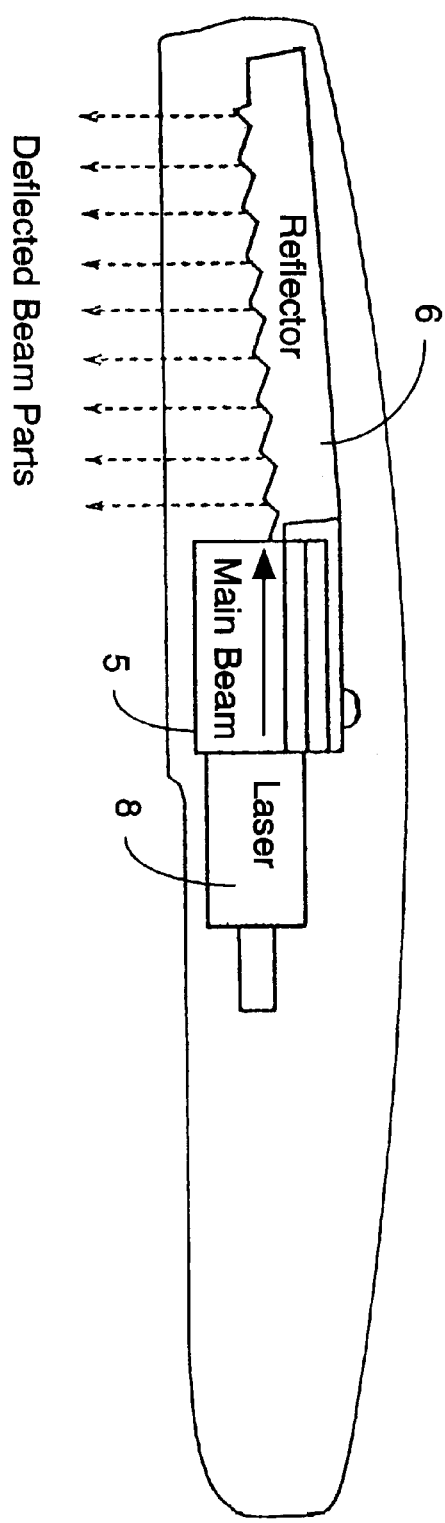
FIG. 2B is a side cutaway view of a preferred embodiment of the device in which the single laser beam is shown being split into several portions which are deflected as a parallel line of laser beams.

FIG. 2B is a cutaway side view of a preferred embodiment of the invention which shows the path of the laser beam across the zigzag edge of the reflector 6. As the laser beam strikes the various steps of the zigzag edge of the reflector 6, portions of the laser beam are distributed as several reflected beam parts which are reflected downward and out through the window 10 toward the furrows formed in the user's hair by the teeth 3. The zigzag reflector 6 provides a substantial advantage to the user in that, since a single laser beam is used, each reflected beam part will have substantially the same amount of energy. This avoids the situation which could happen if multiple lasers were used to generate individual beams, because a multiple laser system could result in hot spots created by any substantial discrepancies in the output power produced by individual lasers.

Figure 3:
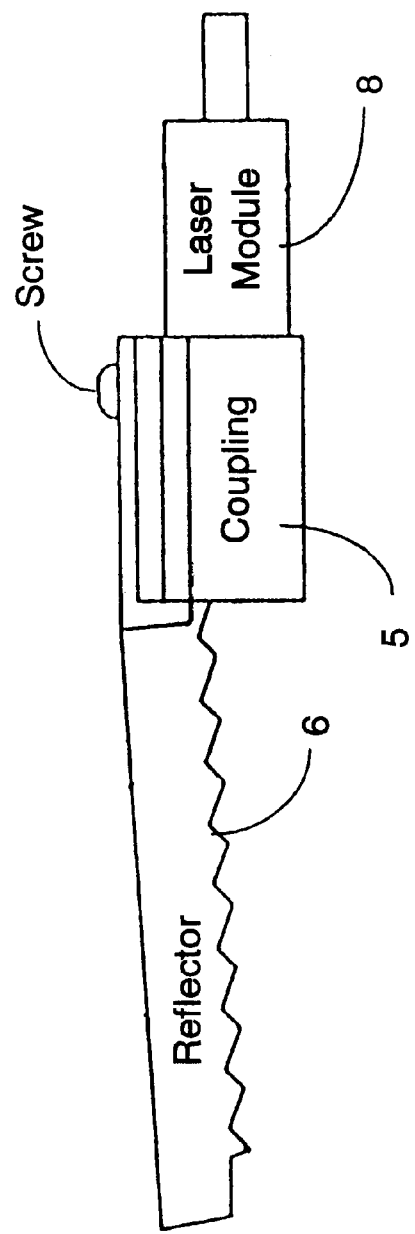
FIG. 3 is a side view of a preferred embodiment of the laser assembling which includes the laser module and the zig-zag beam splitting reflector.

FIG. 3 illustrates the use of a coupling device 5 to align the laser 8 with the reflector 6. This type of mechanical alignment system substantially enhances the ease of manufacture and allows parts to be interchangeable. Further, it eliminates the substantial alignment problems which would occur in a multiple laser system that require each laser to be individually adjusted during manufacture.

Figure 4A:
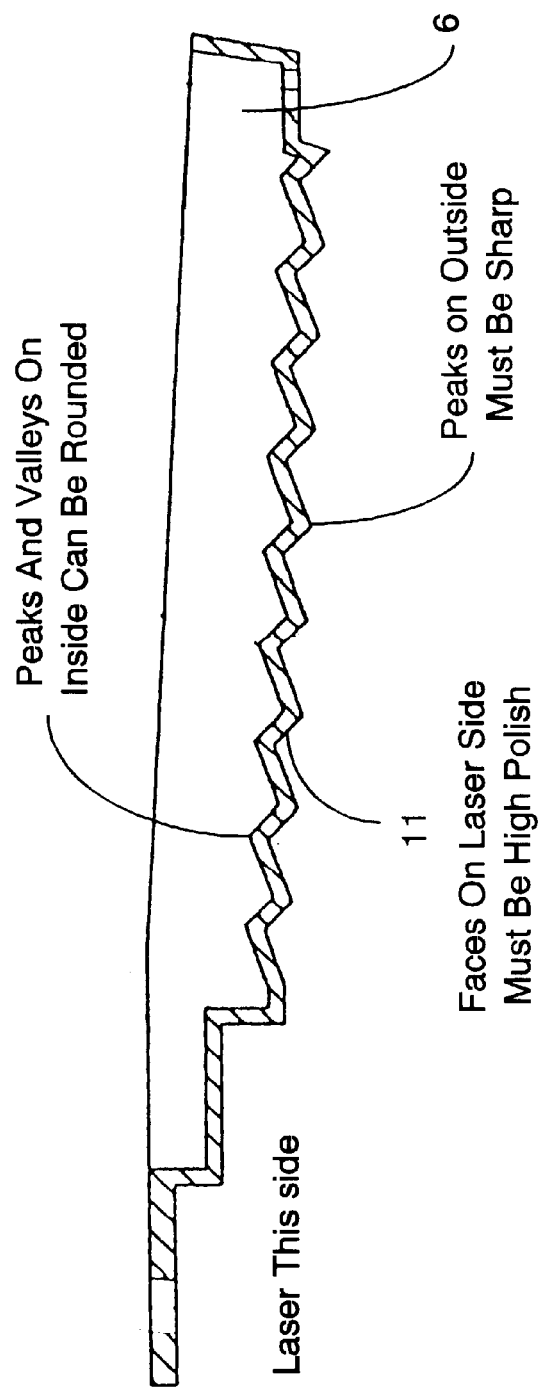
FIG. 4A is a side perspective view of a preferred embodiment of the zigzag beam splitting reflector.

FIG. 4A provides more detail concerning the structure of the reflector 6 which is used in the preferred embodiment. To ensure that the maximum amount of energy is deflected in the proper manner, the face 11 on the reflector 6 which is struck by the laser must have a high polish and reflectivity. While the peaks and valleys on the inside of the reflector 6 can be rounded, the peaks and valleys on the outside of the reflector 6 must be sharp to avoid defusing the laser beams.

Figure 4B:
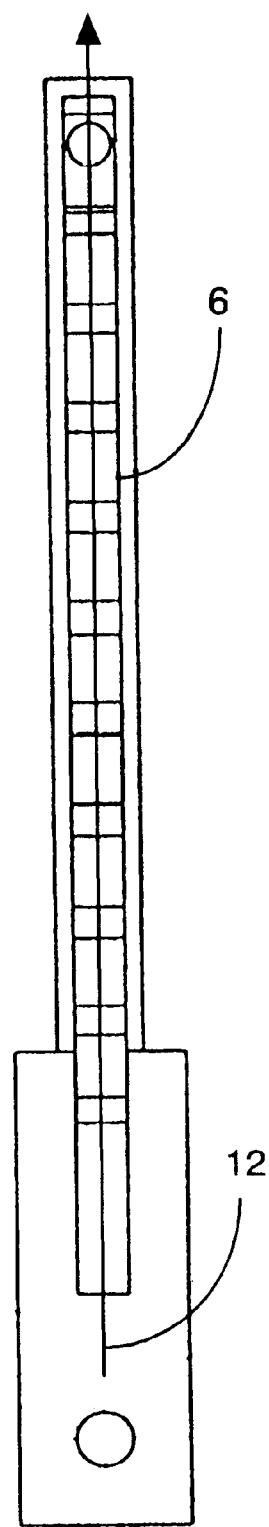
FIG. 4B is a bottom view of a preferred embodiment of the zigzag beam splitting reflector.

In FIG. 4B, a bottom view of the reflector 6 is shown which illustrates the path of the laser beam when it is projected from the laser. The laser beam is directed across the central portion of the reflector 6 to ensure that laser energy is not wasted by projecting some of it past the edge of the reflector 6.

Figure 4C:
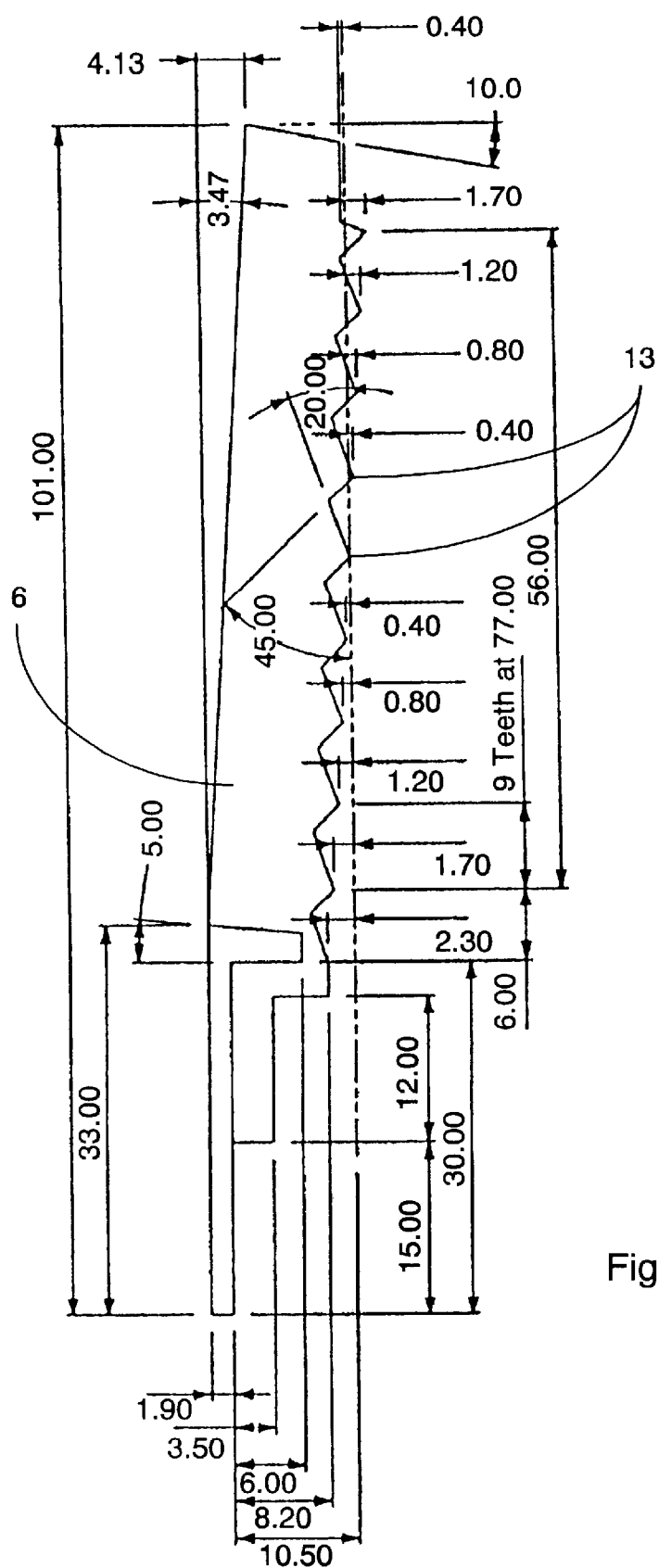
FIG. 4C is an illustration of a preferred embodiment of the arrangement of teeth on the zigzag beam splitting reflector.

FIG. 4C provides more detailed information regarding the structure of the reflector 6. As can be seen in this figure, the zigzag structure of the reflector 6 places steps 13 which are more distant from the laser source at progressively lower elevations such that as the laser beam is projected outward from the laser's lateral path, each step intercepts and deflects a portion of the laser beam. By aligning specific amounts of area to each deflected beam, a uniform distribution of power can be achieved by splitting the single laser beam.

Figure 5A:
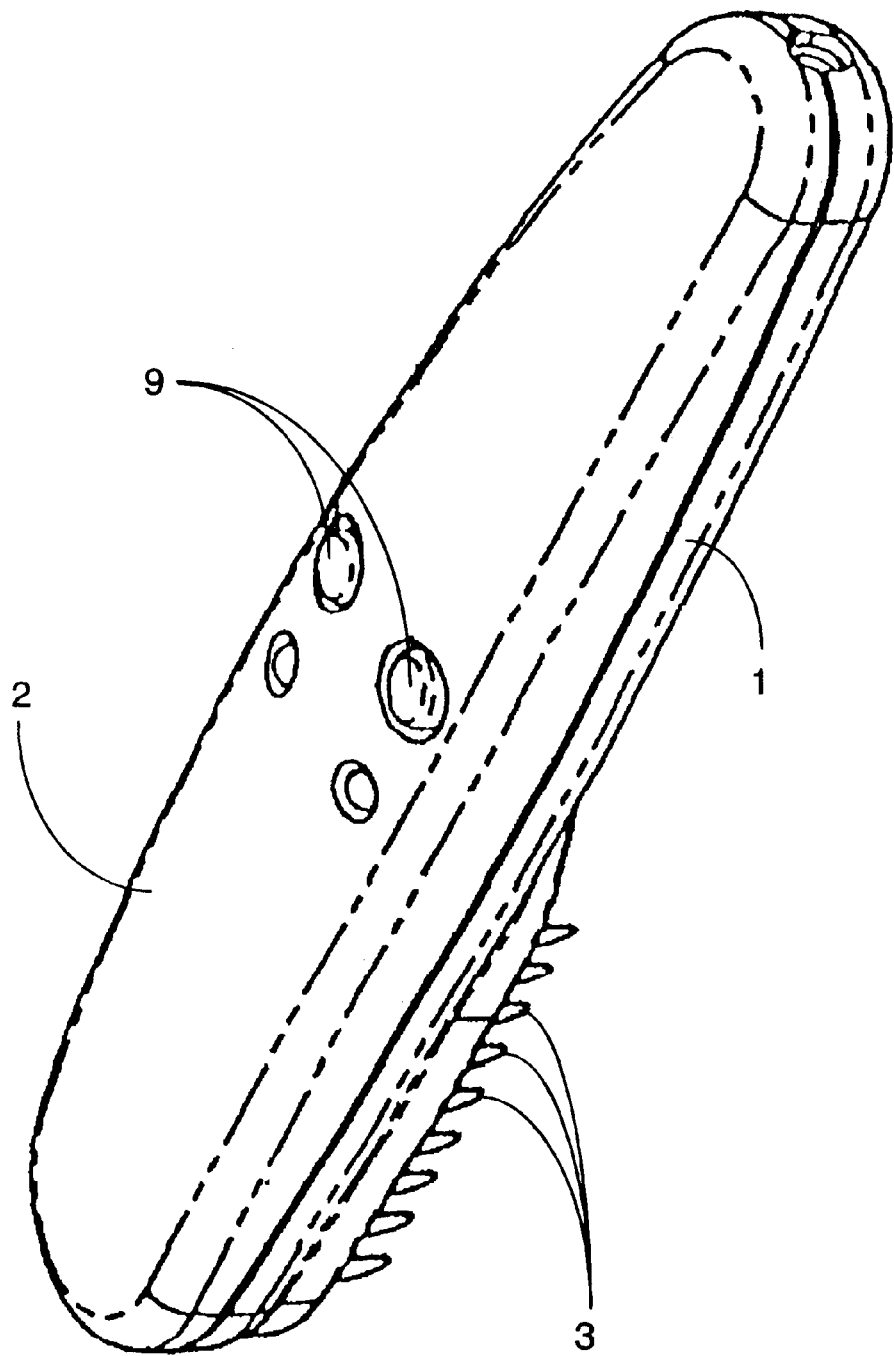
FIG. 5A is a top perspective view of a preferred embodiment of the device which illustrates the control switches on the top of the device and the furrow forming teeth extending from the bottom of the device.

FIG. 5A is a perspective view of a preferred embodiment of the handheld device. In this view, the teeth 3 are shown projecting downward from lower housing 1, and control switches 9 are shown located on the upper housing 2.

Figure 5B:
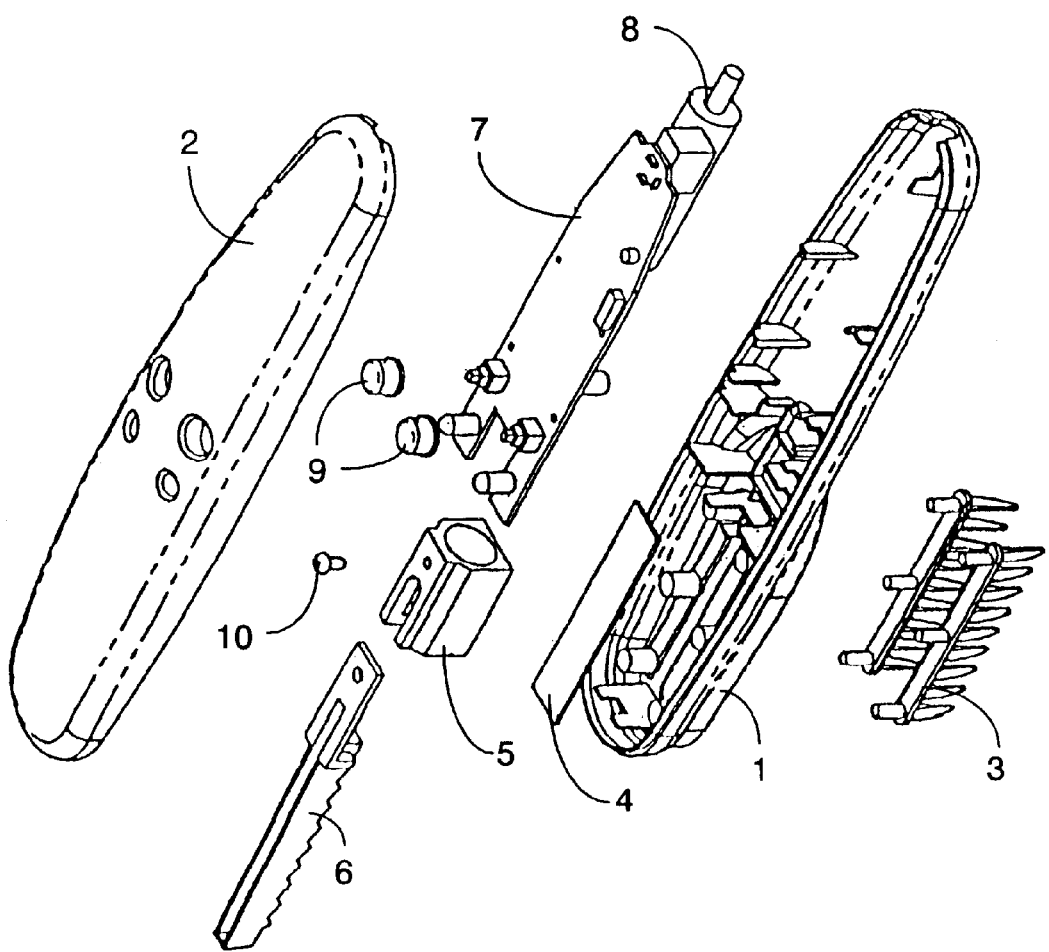
FIG. 5B is an exploded perspective view of a preferred embodiment of the device which illustrates its internal components.

FIG. 5B is an exploded view of the embodiment of FIG. 5A. In this embodiment, the various components of the system can be seen aligned with one another. The laser 8 is shown attached to a printed circuit board 7 which contains the control circuitry. The printed circuit board 7 is used to align the laser 8 with the coupling 5 that attaches to the reflector 6. By properly fabricating the various components of this device, individual alignment of each unit is unnecessary. As a result, manufacturing costs are substantially reduced. Also shown in this figure are lower housing 1, upper housing 2, teeth 3, switch caps 9, window 4, and associated hardware such as screw 10.

Figure 6:
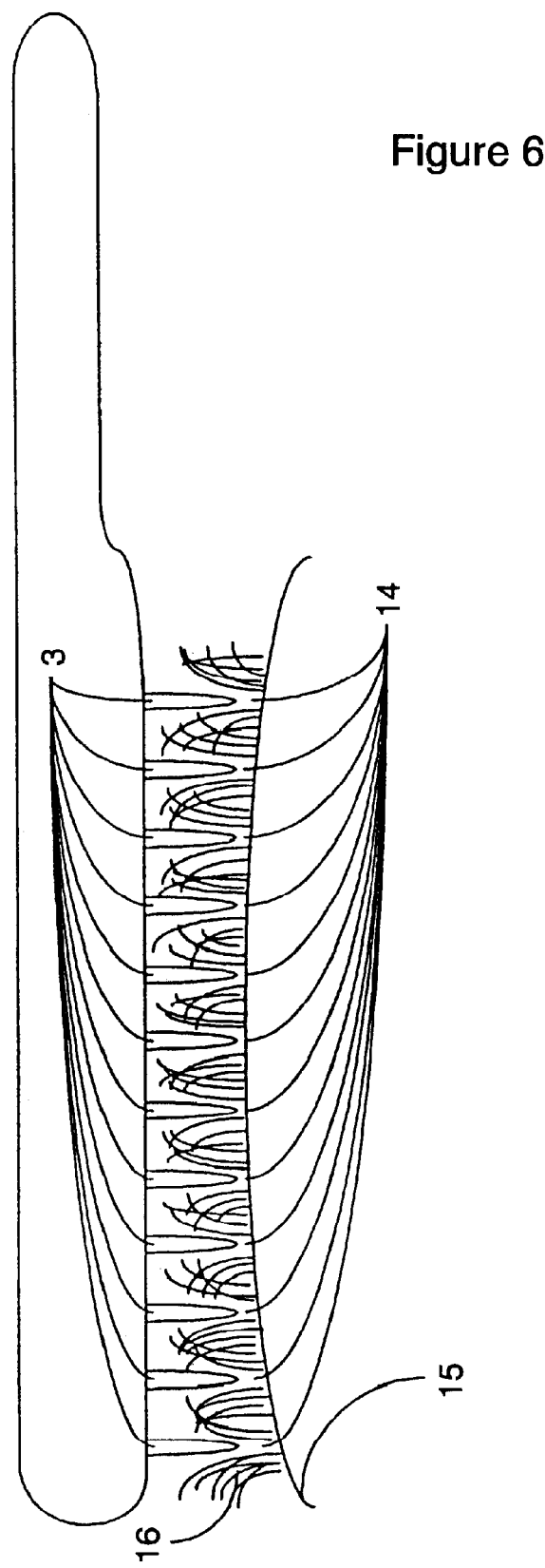
FIG. 6 is an illustration of a preferred embodiment of the device in which an individual's hair is being furrowed to maximize the amount of laser energy applied to the individual's scalp.

FIG. 6 illustrates how the teeth 3 were used to produce furrows 14 in the individual's hair 16. This figure has a side view illustrating the teeth 3 being pulled through the user's hair 16 while in close proximity to the user's scalp 15. As can be seen, the movement of the teeth 3 through the hair 16 pushes the hair 16 aside to form furrows 14. As the hair forms furrows 14, the scalp 15 between the teeth 3 is exposed. Since the laser beam is aligned between the two opposing teeth for each furrow 14, the laser beam is directed to the surface of the scalp 15 which has been exposed by the furrow 14. The advantage provided by furrowing the hair 16 is that a high percentage of the laser energy is effectively applied to the scalp 15, and the hair 16 is prevented from interfering with the application of laser energy to the scalp 15.

While the invention has been described with respect to a preferred embodiment thereof, it will be understood by those skilled in the art that various changes in detail may be made therein without departing from the spirit, scope, and teaching of the invention. For example, the material used to construct the device may be anything suitable, the size and shape of the device can vary, the type of laser can vary, etc. Accordingly, the invention herein disclosed is to be limited only as specified in the following claims.

We claim:

1. A handheld laser hair treatment device, comprising:
a laser assembly, further comprising:
   a laser beam generator;
   a power supply for supplying power to the laser beam generator; and
   means to direct at least one laser beam outward from the laser assembly; and
means to expose the scalp of an individual when the laser treatment device is moved over the individual's scalp such that the laser beam is not obstructed from coming in contact with the scalp by the individual's hair;
whereby the scalp of the individual is exposed during application of energy from the laser beam to the scalp.

2. A device, as in claim 1, wherein:
the laser beam assembly produces a plurality of laser beams, each laser beam spaced apart from one another;
the means to expose the scalp further comprises a first plurality of teeth, each tooth associated with a laser beam and positioned such that when the device is moved across an individual's scalp, each tooth creates a furrow in the hair in front of the laser beam and the laser beam is substantially unobstructed by the individual's hair;
whereby the amount of laser energy reaching the individual's scalp is maximized by the creation of furrows in the individual's hair.

3. A device, as in claim 2, further comprising:
a second plurality of teeth, each tooth in the second plurality of teeth associated with a tooth in the first plurality of teeth such that they form a related pair of teeth which are associated with a laser beam; and
each related pair of teeth are positioned such that the first tooth is positioned ahead of its related laser beam and the second tooth is positioned behind its related laser beam, such that when the device is moved across an individual's scalp, the first tooth creates a furrow for the laser beam and the second tooth holds the furrow open while the laser is moving across the individual's scalp;
whereby the related pairs of teeth hold the furrow open for an extended period of time while the laser beam is being directed to the individual scalp.

4. A device, as in claim 3, wherein:
the laser generator produces a single laser beam; and
a beam splitter is used to split the single laser beam into a plurality of separate laser beams;
whereby the device produces multiple laser beams from a single laser beam generator.

5. A device, as in claim 4, wherein:
the beam splitter is a beam reflector having a zigzag edge having a plurality of teeth, each reflector tooth in the zigzag edge reflecting a portion of the laser beam;
whereby the portions of the laser beam created by the reflector teeth each form an independent laser beam.

6. A device, as in claim 1, wherein:
the laser generator produces a single laser beam; and
a beam splitter is used to split the single laser beam into a plurality of separate laser beams;
whereby the device produces multiple laser beams from a single laser beam generator.

7. A device, as in claim 6, wherein:
the beam splitter is a beam reflector having a zigzag edge having a plurality of teeth, each reflector tooth in the zigzag edge reflecting a portion of the laser beam;
whereby the portions of the laser beam created by the reflector teeth each form an independent laser beam.

8. A handheld laser hair treatment device, comprising:
a laser assembly, further comprising:
   a laser beam generator which generates a laser beam;
   a power supply for supplying power to the laser beam generator; and
a beam splitter for splitting the laser beam into multiple substantially parallel laser beams and to direct the laser beams outward from the laser assembly;
whereby the scalp of the individual is exposed during application of energy from the laser beam to the scalp.

9. A device, as in claim 8, wherein:
the beam splitter is a beam reflector having a zigzag edge with a plurality of reflector teeth, each reflector tooth in the zigzag edge reflecting a portion of the laser beam;
whereby the portions of the laser beam created by the reflector teeth each form an independent laser beam.

10. A device, as in claim 9, further comprising:
a first plurality of furrow teeth, each furrow tooth associated with a laser beam and positioned such that when the device is moved across an individual's scalp, each furrow tooth creates a furrow in the hair in front of the laser beam and the laser beam is substantially unobstructed by the individual's hair;
whereby the amount of laser energy reaching the individual's scalp is maximized by the creation of furrows in the individual's hair.

11. A device, as in claim 10, further comprising:
a second plurality of furrow teeth, each furrow tooth in the second plurality of furrow teeth associated with a tooth in the first plurality of furrow teeth such that they form a related pair of furrow teeth which are associated with a laser beam; and
each related pair of furrow teeth are positioned such that the first tooth is positioned ahead of its related laser beam and the second tooth is positioned behind its related laser beam, such that when the device is moved across an individual's scalp, the first furrow tooth creates a furrow in the individual's hair for the laser beam and the second furrow tooth holds the furrow open while the laser is moving across the individual's scalp;
whereby the related pairs of furrow teeth hold the furrow open for an extended period of time while the laser beam is being directed to the individual's scalp.

12. A method of applying laser energy to an individual scalp, including the steps of:
applying laser energy to the scalp of an individual by moving a handheld laser generator across the individual's scalp; and
maximizing the amount of laser energy applied to the scalp of the individual by deflecting hair away from the scalp of an individual such that the laser energy is not obstructed from coming in contact with the scalp by the individual's hair;

whereby the scalp of the individual is substantially unobstructed by hair during application of energy from the laser energy to the scalp.

13. A method, as in claim 12, including the additional step of:

deflecting the hair away from the path of the laser energy by creating a furrow in the individual's hair prior to passing the laser energy over the portion of the scalp in which the furrow was created.

14. A method, as in claim 13, including the additional step of:

using a plurality of furrow teeth which are associated with the laser energy, and positioned forward of the path of the laser energy, to create furrows by parting the individual's hair prior to passing the laser energy over the individual's scalp.

15. A method, as in claim 14, including the additional step of:

extending the time in which the furrows remain open by using pairs of associated furrow teeth located in the path of the laser energy and positioned in front of and to the rear of the laser energy.

16. A method, as in claim 15, including the additional step of:

extending the surface area covered by the laser energy by splitting a single laser beam into multiple, substantially parallel, laser beams with a beam splitter;

whereby a large total surface area of scalp can be irradiated by a single laser beam.

17. A method, as in claim 16, including the additional step of:

splitting the single laser beam with a multi-toothed beam refractor having a zigzag edge with a plurality of reflector teeth, and reflecting a portion of the single laser beam with each reflector tooth;

whereby the portions of the single laser beam created by the reflector teeth each form an independent laser beam.

18. A method, as in claim 13, including the additional step of:

extending the surface area covered by a single laser beam by splitting the laser beam into multiple, substantially parallel, laser beams with a beam splitter;

whereby a large total surface area of scalp can be irradiated by a single laser beam.

19. A method, as in claim 18, including the additional step of:

splitting the laser beam with a multi-toothed beam refractor having a zigzag edge with a plurality of reflector teeth, and reflecting a portion of the single laser beam with each reflector tooth;

whereby the portions of the single laser beam created by the reflector teeth each form an independent laser beam.

20. A method, as in claim 12, including the additional step of:

extending the surface area covered by the laser energy by splitting a single laser beam into multiple, substantially parallel, laser beams with a beam splitter;

where a the large total surface area of scalp can be irradiated by a single laser beam.

* * * * *

US006497719C1

(12) EX PARTE REEXAMINATION CERTIFICATE (6157th)
United States Patent
Pearl et al.

(10) Number: US 6,497,719 C1
(45) Certificate Issued: Mar. 18, 2008

(54) APPARATUS AND METHOD FOR STIMULATING HAIR GROWTH

(75) Inventors: Henry Pearl, Boca Raton, FL (US); David Sinofsky, Boca Raton, FL (US)

(73) Assignee: Lexington Lasercomb IP AG, St. Gallen (CH)

Reexamination Request:
No. 90/008,121, Jul. 25, 2006

Reexamination Certificate for:
Patent No.: 6,497,719
Issued: Dec. 24, 2002
Appl. No.: 09/882,724
Filed: Jun. 15, 2001

Related U.S. Application Data

(60) Provisional application No. 60/273,701, filed on Mar. 6, 2001.

(51) Int. Cl.
*A61N 5/067* (2006.01)

(52) U.S. Cl. .......................................... 607/89; 607/88
(58) Field of Classification Search ....................... None
See application file for complete search history.

(56) References Cited

U.S. PATENT DOCUMENTS 5,246,019 A 9/1993 Godfrey et al.

6,053,180 A 4/2000 Kwan
6,063,108 A 5/2000 Salansky et al.
6,450,941 B1 9/2002 Larsen

FOREIGN PATENT DOCUMENTS

| AU | 636285 | 4/1993 |
| DE | 91 02 407.2 | 7/1991 |
| DE | G91 02 407.2 | 7/1991 |
| JP | S62-170206 A | 7/1987 |
| JP | S62-170206 | 7/1987 |
| JP | 2-136146 A | 5/1990 |
| JP | 21346146 | 5/1990 |
| JP | 3-228708 | 10/1991 |
| RU | 2114544 | 7/1998 |
| WO | WO 95/19808 | 1/1995 |

*Primary Examiner*—Beverly M. Flanagan

(57) ABSTRACT

A hand-held laser device that stimulates hair growth. The device provides distributed laser light to the scalp while simultaneously parting the user's hair to ensure that the laser light contacts the user's scalp. A unique beam splitting reflector splits a single laser beam to ensure that energy from the laser beam is evenly distributed. The reflector is mechanically aligned with the laser source and has a zigzag structure which mechanically deflects portions of the beam as it passes over the peaks of the reflector. The portions of the laser beam form a line of laser beams that project toward the user's scalp. Parallel rows of teeth are aligned with a central row of individual laser beams and part the user's hair to form furrows in the user's hair as the device is combed through the user's hair. The furrows create an unobstructed path for the laser beam to reach the scalp of the user.

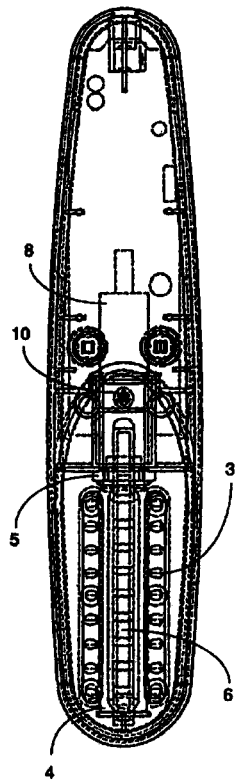

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–4, 7–9, 12–16 and 19 are determined to be patentable as amended.

Claims 5, 6, 10, 11, 17, 18 and 20, dependent on an amended claim, are determined to be patentable.

New claims 21 and 22 are added and determined to be patentable.

1. A handheld laser hair treatment device, comprising:
a laser assembly, further comprising:
  a laser beam generator;
  a power supply for supplying power to the laser beam generator; and
  means to direct at least one laser beam outward from the laser assembly; and
[means] *a plurality of non-laser carrying teeth* to expose the scalp of an individual when the laser treatment device is moved over the individual's scalp such that the laser beam is not obstructed from coming in contact with the scalp by the individual's hair;
whereby the scalp of the individual is exposed during application of energy from the laser beam to the scalp.

2. A device, as in claim 1, wherein:
the laser beam assembly produces a plurality of laser beams, each laser beam spaced apart from one another;
[the means to expose the scalp] *the plurality of non-laser carrying teeth* further comprises a first plurality of *non-laser carrying* teeth, each *non-laser carrying* tooth associated with a laser beam and positioned such that when the device is moved across an individual's scalp, each *non-laser carrying* tooth creates a furrow in the hair in front of the laser beam and the laser beam is substantially unobstructed by the individual's hair;
whereby the amount of laser energy reaching the individual's scalp is maximized by the creation of furrows in the individual's hair.

3. A device, as in claim 2, further comprising:
a second plurality of *non-laser carrying* teeth, each tooth in the second plurality of *non-laser carrying* teeth associated with a tooth in the first plurality of *non-laser carrying* teeth such that they form a related pair of *non-laser carrying* teeth which are associated with a laser beam; and
each related pair of *non-laser carrying* teeth are positioned such that the first *non-laser carrying* tooth is positioned ahead of its related laser beam and the second *non-laser carrying* tooth is positioned behind its related laser beam, such that when the device is moved across an individual's scalp, the first *non-laser carrying* tooth creates a furrow for the laser beam and the second *non-laser carrying* tooth holds the furrow open while the laser is moving across the individual's scalp;
whereby the related pairs of *non-laser carrying* teeth hold the furrow open for an extended period of time while the laser beam is being directed to the individual scalp.

4. [A device, as in claim 3,] *A handheld laser hair treatment device, comprising:*
*a laser assembly, further comprising:*
  *a laser beam generator;*
  *a power supply for supplying power to the laser beam generator; and*
  *means to direct at least one laser beam outward from the laser assembly; and*
  *means to expose the scalp of an individual when the laser treatment device is moved over the individual's scalp such that the laser beam is not obstructed from coming in contact with the scalp by the individual's hair;*
*whereby the scalp of the individual is exposed during application of energy from the laser beam to the scalp;*
*wherein the laser beam produces a plurality of laser beams, each laser beam spaced apart from one another;*
  *the means to expose the scalp further comprises a first plurality of teeth, each tooth associated with a laser beam and positioned such that when the device is moved across an individual's scalp, each tooth creates a furrow in the hair in front of the laser beam and the laser beam is substantially unobstructed by the individual's hair;*
  *whereby the amount of laser energy reaching the individual's scalp is maximized by the creation of furrows in the individual's hair; and*
*further comprising:*
  *a second plurality of teeth, each tooth in the second plurality of teeth associated with a tooth in the first plurality of teeth such that they form a related pair of teeth which are associated with a laser beam; and*
  *each related pair of teeth are positioned such that the first tooth is positioned ahead of its related laser beam and the second tooth is positioned behind its related laser beam, such that when the device is moved across an individual's scalp, the first tooth creates a furrow for the laser beam and the second tooth holds the furrow open while the laser is moving across the individual's scalp;*
  *whereby the related pairs of teeth hold the furrow open for an extended period of time while the laser beam is being directed to the individual scalp;*
*wherein:*
  *the laser generator produces a single laser beam; and*
  *a beam splitter is used to split the single laser beam into a plurality of separate laser beams;*
  *whereby the device produces multiple laser beams from a single laser beam generator.*

7. [A device, as in claim 6, ] *A handheld laser hair treatment device, comprising:*
*a laser assembly, further comprising:*
  *a laser beam generator;*
  *a power supply for supplying power to the laser beam generator; and*
  *means to direct at least one laser beam outward from the laser assembly; and*
  *means to expose the scalp of an individual when the laser treatment device is moved over the individual's* scalp such that the laser beam is not obstructed from coming in contact with the scalp by the individual's hair;

whereby the scalp of the individual is exposed during application of energy from the laser beam to the scalp;

wherein:
the laser generator produces a single laser beam; and a beam splitter is used to split the single laser beam into a plurality of separate laser beams;

whereby the device produces multiple laser beams from a single laser beam generator and wherein:
the beam splitter is a beam reflector having a zigzag edge having a plurality of teeth, each reflector tooth in the zigzag edge reflecting a portion of the laser beam;

whereby the portions of the laser beam created by the reflector teeth each form an independent laser beam.

8. A handheld laser hair treatment device, comprising:
a laser assembly, further comprising:
a laser beam generator which generates a laser beam;
a power supply for supplying power to the laser beam generator; [and]
a beam splitter for splitting the laser beam into multiple substantially parallel laser beams and to direct the laser beams outward from the laser assembly;
*and a plurality of a non-laser carrying teeth;* whereby the scalp of the individual is exposed during application of energy from the laser beam to the scalp *by the non-laser carrying teeth.*

9. [A device, as in claim 8,] *A handheld laser hair treatment device, comprising:*

*a laser assembly, further comprising:*
*a laser beam generator which generates a laser beam;*
*a power supply for supplying power to the laser beam generator; and*
*a beam splitter for splitting the laser beam into multiple substantially parallel laser beams and to direct the laser beams outward from the laser assembly;*
*whereby the scalp of the individual is exposed during application of energy from the laser beam to the scalp;* wherein:
the beam splitter is a beam reflector having a zigzag edge with a plurality of reflector teeth, each reflector tooth in the zigzag edge reflecting a portion of the laser beam;

whereby the portions of the laser beam created by the reflector teeth each form an independent laser beam.

12. A method of applying laser energy to an individual scalp, including the steps of:
applying laser energy to the scalp of an individual by moving a handheld laser generator across the individual's scalp; and
maximizing the amount of laser energy applied to the scalp of the individual by deflecting hair away from the scalp of an individual *with a plurality of non-laser carrying teeth* such that the laser energy is not obstructed from coming in contact with the scalp by the individual's hair;
whereby the scalp of the individual is substantially unobstructed by hair during application of energy from the laser energy to the scalp.

13. A method, as in claim 12, including an additional step of:

deflecting the hair away from the path of the laser energy by creating a furrow in the individual's hair *with a plurality of non-laser carrying teeth* prior to passing the laser energy over the portion of the scalp in which the furrow was created.

14. A method, as in claim 13, including the additional step of:

using a plurality of *non-laser carrying* furrow teeth which are associated with the laser energy, and positioned forward of the path of the laser energy, to create furrows by parting the individual's hair prior to passing the laser energy over the individual's scalp.

15. A method, as in claim 14, including the additional step of:

extending the time in which the furrows remain open by using pairs of associated *non-laser carrying* furrow teeth located in the path of the laser energy and positioned in front of and to the rear of the laser energy.

16. [A method, as in claim 15,] *A method of applying laser energy to an individual scalp, including the steps of:*

*applying laser energy to the scalp of an individual by moving a handheld laser generator across the individual's scalp; and*

*maximizing the amount of laser energy applied to the scalp of the individual by deflecting hair away from the scalp of an individual such that the laser energy is not obstructed from coming in contact with the scalp by the individual's hair;*

*whereby the scalp of the individual is substantially unobstructed by hair during application of energy from the laser energy to the scalp;*

*including the additional step of:*
*deflecting the hair away from the path of the laser energy by creating a furrow in the individual's hair prior to passing the laser energy over the portion of the scalp in which the furrow was created;*

*including the additional step of:*
*using a plurality of furrow teeth which are associated with the laser energy, and positioned forward of the path of the laser energy, to create furrows by parting the individual's hair prior to passing the laser energy over the individual's scalp;*

*including the additional step of:*
*extending the time in which the furrows remain open by using pairs of associated furrow teeth located in the path of the laser energy and positioned in front of and to the rear of the laser energy; and* including the additional step of:
extending the surface area covered by the laser energy by splitting a single laser beam into multiple, substantially parallel, laser beams with a beam splitter;
whereby a large total surface area of scalp can be irradiated by a single laser beam.

19. [A method, as in claim 18,] *A method of applying laser energy to an individual scalp, including the steps of:*

*applying laser energy to the scalp of an individual by moving a handheld laser generator across the individual's scalp; and*

*maximizing the amount of laser energy applied to the scalp of the individual by deflecting hair away from the scalp of an individual such that the laser energy is not obstructed from coming in contact with the scalp by the individual's hair;*

*whereby the scalp of the individual is substantially unobstructed by hair during application of energy from the laser energy to the scalp;* including the additional step of:
deflecting the hair away from the path of the laser energy by creating a furrow in the individual's hair prior to passing the laser energy over the portion of the scalp in which the furrow was created;

including the additional step of:
extending the surface area covered by a single laser beam by splitting the laser beam into multiple, substantially parallel, laser beams with a beam splitter;

whereby a large total surface area of scalp can be irradiated by a single laser beam; and including the additional step of:
splitting the laser beam with a mult-toothed beam refractor having a zigzag edge with a plurality of reflector teeth, and reflecting a portion of the single laser beam with each reflector tooth;

whereby the portions of the single laser beam created by the reflector teeth each form an independent laser beam.

21. A handheld laser hair treatment device, comprising:
a laser assembly, further comprising:
a laser beam generator;
a power supply for supplying power to the laser beam generator; and
means to project at least one laser beam outward from the laser assembly toward an individual's scalp; and
non-laser carrying teeth to expose the scalp of an individual when the laser treatment device is moved over the individual's scalp by deflecting the individual's hair away from the path of the laser beam with the non-laser carrying teeth that part the hair to create an open light path in the individual's hair in advance of the passing laser beam such that the laser beam is not obstructed from coming in contact with the scalp by the individual's hair;

whereby the scalp of the individual is exposed during application of energy from the laser beam to the scalp.

22. A method of applying laser energy to an individual scalp, including the steps of:
applying laser energy to an individual's scalp by moving a handheld laser generator across the individual's scalp; and
maximizing the amount of laser energy applied to the individual's scalp by deflecting hair away from the path of the laser energy with non-laser carrying teeth such that the hair is parted in front of the laser energy such that the laser energy is not obstructed from coming in contact with the scalp by the individual's hair;

whereby the scalp of the individual is substantially unobstructed by hair during application of energy from the laser energy to the scalp.

\* \* \* \* \*